United States Patent [19]

Vandeventer et al.

[11] Patent Number: 5,097,093

[45] Date of Patent: Mar. 17, 1992

[54] INBRED CORN LINE PHJ33

[75] Inventors: Walter E. Vandeventer, Tipton; Joseph W. Keaschall, Sharpsville, both of Ind.

[73] Assignee: Pioneer Hi-Bred International, Inc., Des Moines, Iowa

[21] Appl. No.: 402,026

[22] Filed: Aug. 30, 1989

[51] Int. Cl.$^5$ .................. A01H 5/00; A01H 4/00; C12N 5/04

[52] U.S. Cl. .................. 800/200; 800/250; 800/DIG. 56; 435/240.4; 435/240.49; 435/240.50

[58] Field of Search ....... 800/200, 250, 205, DIG. 56; 47/58, DIG. 1; 435/240.4, 240.49, 240.50

[56] References Cited

U.S. PATENT DOCUMENTS 4,812,600  3/1989  Jensen .................. 800/1

OTHER PUBLICATIONS

Duncan et al., "The Production of Callus Capable of Plant Regeneration from Immature Embryos of Numerous Zea mays Genotypes", Planta (1985) 165:322-332.
Songstad et al., "Effect of ACC (1-aminocyclopropane-1-carboxylic acid), Silver Nitrate, and Norbornadiene on Plant Regeneration from Maize Callus Cultures", Plant Cell Reports 7:262-265 (1988).
K. V. Rao et al., "Somatic Embryogenesis in Glume Callus Cultures", Maize Genetics Cooperation Newsletter (1986), vol. 60.
Conger, B. V. et al., "Somatic Embryogenesis from Cultured Leaf Segments of Zea Mays", Plant Cell Reports 6:345-347 (1987).
Bates (1974), Dept. Gr Scik State U. Mahattan U.S.A. Londres Mexico; Cinmyt (Abs).
Galinat (1977) In/Corn & Corn Improv. Ed. Sprogue, ASA, Inc. Pub. Madison Wis., pp. 1 & 35.
Sprague et al., (1972) In/Corn & Corn Improv. Ed. Sprague, ASA Publ. Inc. Madison Wis., p. 316.
Howacki et al., (1972), Bull. de L'Acad. Blenaise de Sci., vol. XX, #10, pp. 695-698.
Green et al (1982), In/Maize for Biol. Res. Ed. for W. F. Shenden, pp. 367-372, Ph. Mol. Biol. Ass. U. Press McDohota.
Germplom Res. Info. Met. (1960), Zen Mays PI 262587.
Germplom Res. Inf. Met. (1971) Zea Mays PI 360877.
Germplom, Res. Inf. Met. (1950), Zea Mays PI 181989.
Sass (1977), "Morphology", In/Corn & Corn Improvement Editor G. F. Sprague, ASA Publications Madison Wis. U.S.A.

Primary Examiner—Howard J. Locker
Assistant Examiner—Gary Benzion
Attorney, Agent, or Firm—Michael J. Roth

[57] ABSTRACT

According to the invention, there is provided an inbred corn line, designated PHJ33. This invention thus relates to the plants and seeds of inbred corn line PHJ33 and to methods for producing a corn plant produced by crossing the inbred line PHJ33 with itself or with another corn plant. This invention further relates to hybrid corn seeds and plants produced by crossing the inbred line PHJ33 with another corn line or plant and to crosses with related species.

6 Claims, No Drawings

INBRED CORN LINE PHJ33

FIELD OF THE INVENTION

This invention is in the field of corn breeding specifically relating to an inbred corn line designated PHJ33.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (Zea mays L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding for single-gene traits starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of any individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

SUMMARY OF THE INVENTION

According to the invention, there is provided a novel inbred corn line, designated PHJ33. This invention thus relates to the seeds of inbred corn line PHJ33, to the plants of inbred corn line PHJ33, and to methods for producing a corn plant produced by crossing the inbred line PHJ33 with itself or another corn line. This invention further relates to hybrid corn seeds and plants produced by crossing the inbred line PHJ33 with another corn line or a related species.

DEFINITIONS

In the description and examples that follow, a number of terms are used herein. In order to provide a clear and consistent understanding of the specification and claims, including the scope to be given such terms, the following definitions are provided:

BAR PLT = BARREN PLANTS. This is the number of plants per plot that were not barren (lack ears).

BRT STK = BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR = YIELD (BUSHELS/ACRE). Actual yield of the grain at harvest adjusted to 15.5% moisture. ABS is in absolute terms and % MN is percent of the mean for the experiments in which the inbred or hybrid was grown.

CLD TST = COLD TEST. This is the percentage of kernels that germinate under cold soil conditions. ABS = absolute measurement and % MN is percentage of mean of the experiments in which inbred or hybrid was grown.

COB SC = COB SCORE. The cob score is a rating of how well the grain is shelled off the cob and how badly the cob is broken up going through the combine. This is given as a 1 to 9 score with 9 being very good. A high score indicates that the grain shells off of the cob well, and the cob does not break.

DRP EAR = DROPPED EARS. This is a measure of the number of dropped ears per plot and represents the percentage of plants that did not drop ears prior to harvest.

EAR HT = EAR HEIGHT. The ear height is a measure from the ground to the top developed ear node attachment and is measured in inches.

EAR SZ = EAR SIZE. A 1 to 9 visual rating of ear size. The higher the rating the larger the ear size.

EST CNT = EARLY STAND COUNT. This is a measure of the stand establishment in the spring and represents the number of plants that emerge on a per plot basis for the inbred or hybrid.

GDU SHD = GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(Max.\ temp. + Min.\ temp)}{2} - 50$$

The highest maximum temperature used is 86° F. and the lowest minimum temperature used is 50° F. For each inbred or hybrid it takes a certain number of GDUs to reach various stages of plant development.

GDU SLK = GDU TO SILK. The number of growing degree units required for an inbred line or hybrid to have approximately 50 percent of the plants with silk emergence from time of planting. Growing degree units are calculated by the Barger Method as given in GDU SHD definition.

GRN QUL = GRAIN QUALITY. This is a 1 to 9 rating for the general quality of the shelled grain as it is harvested based on such factors as the color of the harvested grain, any mold on the grain, and any cracked grain. High scores indicate good grain quality.

KER LB = KERNELS PER POUND. This is the number of kernels per 0.1 pound.

KSZ L = KERNEL SIZE LARGE. Percentage by weight of shelled corn that passes through a screen with 25/64 inch diameter openings but does not pass through a screen with 22/64 inch diameter openings.

KSZ MF = KERNEL SIZE MEDIUM FLAT. Percentage by weight of shelled corn that passes through a screen with 22/64 inch diameter openings and a screen with 13/64 inch wide slot screen but does not pass through a screen with 18.5/64 inch diameter openings.

KSZ MR = KERNEL SIZE MEDIUM ROUND. Percentage by weight of shelled corn that passes through a screen with 22/64 inch diameter openings but does not pass through a 13/64 inch wide slot screen or a screen with 18.5/64 inch diameter openings.

KSZ S = KERNEL SIZE SMALL. Percentage by weight of shelled corn that passes through a screen with 18.5/64 inch diameter openings but does not through a screen with 16/64 inch diameter openings.

KSZ TIP = KERNEL SIZE TIPS. Percentage by weight of shelled corn that passes through a screen with 16/64 inch diameter openings.

KSZ XL = KERNEL SIZE EXTRA LARGE. Percentage by weight of shelled corn that does not pass through a screen with 5/64 inch diameter openings.

MST = HARVEST MOISTURE. The moisture is the actual percentage moisture of the grain at harvest.

PLT HT = PLANT HEIGHT. This is a measure of the height of the plant from the ground to the tip of the tassel in inches.

POL WT = POLLEN WEIGHT. This is the weight of pollen per 100 plants taken on a plot basis. ABS refers to data in absolute, and % MN refers to data presented as percentage of experimental mean.

PRM = PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG = ROOT LODGING. Root lodging is the percentage of plants that do not root lodge; plants that lean from the vertical axis at an approximately 30° angle or greater would be counted as root lodged.

SCT GRN = SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT—NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT UNADJUSTED. The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

CLN=Corn Lethal Necrosis (MCMV=Maize Chlorotic Mottle Virus and MDMV=Maize Dwarf Mosaic Virus): Visual rating (1-9 score) where a "1" is very susceptible and a "9" is very resistant.

MDM CPX=Maize Dwarf Mosaic Complex (MDMV=Maize Dwarf Mosaic Virus & MCDV=Maize Chlorotic Dwarf Virus): Visual rating (1-9 score) where a "1" is very susceptible and a "9" is very resistant.

COM SMT=Common Smut (Ustilago maydis): Percentage of plants that did not have infection.

ANT ROT=Anthracnose Stalk Rot (Colletotrichum graminicola): Visual rating (1-9 score) where a "1" is very susceptible and a "9" is very resistant.

SLF BLT=Southern Leaf Blight (Bipolaris maydis, Helminthosporium maydis): Visual rating (1-9 score) where a "1" is very susceptible and a "9" is very resistant.

NLF BLT=Northern Leaf Blight (Exserohilum turcicum, H. turcicum): Visual rating (1-9 score) where a "1" is very susceptible and a "9" is very resistant.

HC BLT=Helminthosporium Carbonum Leaf Blight (Bipolariszeicola, H. carbonum): Visual rating (1-9 score) where a "1" is very susceptible and a "9" is very resistant.

COM RST=Common Rust (Puccinia sorghi): Visual rating (1-9 score) where a "1" is very susceptible and a "9" is very resistant.

SO RST=Southern Rust (Puccinia polysora): Visual rating (1-9 score) where a "1" is very susceptible and a "9" is very resistant.

EYE SPT=Eyespot (Kabatiella zeae): Visual rating (1-9 score) where a "1" is very susceptible and a "9" is very resistant.

GLF SPT=Gray Leaf Spot (Cercospora zeae-maydis): Visual rating (1-9 score) where a "1" is very susceptible and a "9" is very resistant.

STW WLT=Stewart's Wilt (Erwinia stewartii): Visual rating (1-9 score) where a "1" is very susceptible and a "9" is very resistant.

GOS WLT=Goss's Wilt (Corynebacterium nebraskense): Visual rating (1-9 score) where a "1" is very susceptible and a "9" is very resistant.

HD SMT=Head Smut (Spacelotheca reiliana): Percentage of plants that did not have infection.

DNY MIL=Downy Mildew (Peronosclerospora sorghi): Percentage of plants that did not have infection.

FUS EAR=Fusarium Ear Mold (Fusarium moniliforme): Percentage of plants that did not have infection.

EAR MLD=General Ear Mold: Visual rating (1-9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (Ostrinia nubilalis): Percentage of plants that did not drop ears under second brood corn borer infestation.

ECB 2SC=European Corn Borer Second Brood (Ostrinia nubilalis): Visual rating (1-9 score) of post flowering damage due to infestation by European Corn Borer. A "1" is very susceptible and a "9" is very resistant.

ECB 1LF=European Corn Borer First Brood (Ostrinia nubilalis): Visual rating (1-9 score) of pre-flowering leaf feeding by European Corn Borer. A "1" is very susceptible and a "9" is very resistant.

ECB 2IT=European Corn Borer Second Brood Tunneling (Ostrinia nubilalis): The average inches of tunneling in the stalk due to second brood (post-flowering) European Corn Borer infestation. Determined by splitting stalks with a knife, from four internodes above the ear to the ground.

DETAILED DESCRIPTION OF THE INVENTION

Inbred Corn Line PHJ33 is a yellow, dent corn inbred with superior characteristics and provides an excellent male parental line in crosses for producing first generation $F_1$ corn hybrids. This inbred is best adapted over the Eastern and Central regions of the United States. The inbred can be used to produce hybrids from approximately 115-130 relative maturity based on the Minnesota Relative Maturity Rating System for harvest moisture of grain. PHJ33 is not acceptable as a female parent because of its large grain size and questionable cold test. As a male, the inbred has heavy pollen shed and should be an excellent male parent. PHJ33 was 130% of the experiment mean for amount of pollen based on the pollen yield test averaged over 8 locations.

The inbred has shown uniformity and stability within the limits of environmental influence for all the traits as described in the Variety Description Information (Table 1) that follows. Most of the data in the Variety Description Information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHJ33.

Inbred corn line PHJ33, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE
PHJ33
VARIETY DESCRIPTION INFORMATION

Type: Dent    Region Best Adapted: East & Central

A. Maturity: Average across maturity zones. Zone: 0
  INBRED = PHJ33
  Heat Unit Shed: 1470
  Heat Unit Silk: 1540
  No. Reps: 47

$$\text{HEAT UNITS} = \frac{[\text{Max. Temp. } (\leq 86° F.) + \text{Min. Temp. } (\geq 50° F.)]^*}{2} - 50$$

B. Plant Characteristics:
  Plant height (to tassel tip): 217 cm
  Length of top ear internode: 11 cm
  Number of ears per stalk: Single
  Ear height (to base of top ear): 93 cm
  Number of tillers: None
  Cytoplasm type: Normal C. Leaf:
  Color: (WF9) Medium green
  Angle from Stalk: 30–60 degrees
  Marginal Waves: (WF9) Few
  Number of Leaves (mature plants): 18
  Sheath Pubescence: (W22) Light
  Longitudinal Creases: (OH56A) Few
  Length (Ear node leaf): 70 cm
  Width (widest point, ear node leaf): 8 cm D. Tassel:
  Number lateral branches: 10
  Branch Angle from central spike: 30–40 degrees
  Pollen Shed: Heavy based on pollen Yield Test (130% of experiment mean)
  Peduncle Length (top leaf to basal branches): 25 cm
  Anther Color: Reddish purple
  Glume Color: Green E. Ear (Husked Ear Data Except When Stated Otherwise):
  Length: 18 cm
  Weight: 120 gm
  Mid-point Diameter: 46 mm
  Silk Color: Greenish Yellow
  Husk Extension (Harvest stage): Medium (Barely covering ear)
  Husk Leaf: Long (>15 cm)
  Taper of Ear: Slight taper
  Position of Shank (dry husks): Upright
  Kernel Rows: Straight, Distinct, Number = 12

TABLE-continued
PHJ33
VARIETY DESCRIPTION INFORMATION

Type: Dent    Region Best Adapted: East & Central

Husk Color (fresh): Light green
  Husk Color (dry): Buff
  Shank Length: 11 cm
  Shank (No. of internodes): 8

F. Kernel (Dried):
  Size (from ear mid-point)
  Length: 10 mm
  Width: 8 mm
  Thick: 5 mm
  Shape Grade (% rounds): No Data
  Pericarp Color: Colorless
  Aleurone Color: Homozygous Yellow
  Endosperm Color: Yellow
  Endosperm Type: Normal
  Gm Wt/100 Seeds (unsized): 27 gm G. Cob:
  Diameter at mid-point: 31 mm
  Strength: Strong
  Color: Pinkish Red H. Diseases:
  Corn Lethal Necrosis (MCMV = Maize Chlorotic Mottle Virus and MDMV = Maize Dwarf Mosaic Virus): Intermediate Maize Dwarf Mosaic Complex (MDMV & MCDV = Maize Chlorotic Dwarf Virus): Susceptible
  Anthracnose Stalk Rot (*C. Graminicola*): Intermediate
  S. Leaf Blight (*H. Maydis*): Resistant
  N. Leaf Blight (*H. Turcicum*): Intermediate
  Carbonum Leaf Blight (*H. Carbonum*): Resistant
  Common Rust (*P. Sorghi*): Intermediate
  Eye Spot (*K. Zeae*): Intermediate
  Gray Leaf Spot (*C. Zeae*): Intermediate
  Stewarts Wilt (*E. Stewartii*): Intermediate
  Goss's Wilt (*C. Nebraskense*): Resistant
  Common Smut (*U. Maydis*): Resistant
  Head Smut (*S. Reiliana*): Resistant
  Downy Mildew (*S. Sorghi*): Intermediate
  Fusarium Ear Mold (*F. Moniliforme*): Susceptible I. Insects:
  ECB1LF European Corn Borer-1 Leaf Damage (Pre-flowering): Intermediate
  ECB2SC European Corn Borer-2 (Post-flowering): Susceptible J. Variety Most Closely Resembling:

| Character | Inbred |
|---|---|
| Maturity | PHV78 |
| Usage | PHV78 |

*If maximum is greater than 86 degrees fahrenheit, then 86 is used and if minimum is less than 50, then 50 is used. Heat units accumulated daily and can not be less than 0.

PHV78 (PVP Certificate No. 8800003, U.S. Pat. No. 4,812,599) is a Pioneer Hi-Bred International, Inc. proprietary inbred.

Items B, C, D, E, F, and G are based primarily on three reps at Johnston, Iowa in 1987 and 1988, plus description information from the maintaining station.

TABLE 2
ELECTROPHORESIS RESULTS
Isozyme Genotypes for PHJ33

Isozyme data was generated for inbred corn line PHJ33 according to the procedure described in Goodman, M. M. and Stuber, C. M., "Genetic identification of lines and crosses using isoenzyme electrophoresis," Proceedings of the Thirty-Fifth Annual Corn and Sorghum Industry Research Conference, Chicago, Illinois (1980).

Alleles Present

| Loci | PHJ33 |
|---|---|
| ACP1 | 2 |
| ADH1 | 4 |
| CAT3 | 9 |
| DIA1 | 8 |
| GOT1 | 4 |

TABLE 2-continued

ELECTROPHORESIS RESULTS
Isozyme Genotypes for PHJ33
Isozyme data was generated for inbred corn line PHJ33 according to the procedure described in Goodman, M. M. and Stuber, C. M., "Genetic identification of lines and crosses using isoenzyme electrophoresis," Proceedings of the Thirty-Fifth Annual Corn and Sorghum Industry Research Conference, Chicago, Illinois (1980).

Alleles Present

| Loci | PHJ33 |
| --- | --- |
| GOT2 | 4 |
| GOT3 | 4 |
| IDH1 | 4 |
| IDH2 | 6 |
| MDH1 | 6 |
| MDH2 | 3.5 |
| MDH3 | 18 |
| MDH4 | 12 |
| MDH5 | 12 |
| MMM | 4 |
| PGM1 | 9 |
| PGM2 | 4 |
| PGD1 | 3.8 |
| PGD2 | 5 |
| PHI1 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHJ33. Further, both first and second parent corn plants can come from the inbred corn line PHJ33. Thus, any such methods using the inbred corn line PHJ33 are part of this invention: selfing, backcrosses, hybrid production, crosses to populations, and the like. All plants produced using inbred corn line PHJ33 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottsville, Va. 1982, at 367–372. Thus, another aspect of this invention is to provide cells which upon growth and differentiation produce the inbred line PHJ33.

The utility of inbred line PHJ33 also extends to crosses with other species. Commonly, suitable species will be of the family Graminaceae, and especially of the genera Zea, Tripsacum, Coix, Schlerachne, Polytoca, Chionachne, and Trilobachne, of the tribe Maydeae. Of these, Zea and Tripsacum, are most preferred. Potentially suitable for crosses with PHJ33 may be the various varieties of grain sorghum, *Sorghum bicolor* (L.) Moench.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHJ33, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE

INBRED AND HYBRID PERFORMANCE OF PHJ33

In the examples that follow the traits and characteristics of inbred corn line PHJ33 are given as a line and in hybrid combination. The data collected on inbred corn line PHJ33 is presented for the key characteristics and traits.

The results in Table 3 compare PHJ33 to PHV78. PHV78 PVP Certificate #8800003, U.S. Pat. No. 4,812,599) is an important inbred that would be widely used in the same area as PHJ33 and would cross well with some of the same inbred lines. This data has been collected over two years of research testing. The results show that the two lines differ significantly for a number of traits. PHJ33 is an earlier maturing inbred requiring 116 fewer GDU's to pollen shed and is shorter than inbred PHV78. PHJ33 is also more resistant to Southern leaf blight and Gray leaf spot than PHV78. PHJ33's disease tolerance makes it an important inbred in the eastern Corn Belt.

The results in Table 4 compare PHJ33 to PHV78 crossed to the same inbred tester. This data was collected in the Eastern and Central Corn Belt. The results show that the two lines differ significantly for a number of traits in hybrid combination. The PHJ33 hybrid showed a lower moisture level at harvest, had earlier pollen shed than the PHV78 hybrids and showed greater resistance to root lodging than the PHV78 hybrid. PHJ33 has given good performance in specific hybrid combinations.

The results in Table 5 compare a PHJ33 hybrid to Pioneer ® brand 3324. These hybrids have a parent in common that is not PHJ33 Pioneer ® brand 3324 is a hybrid grown in most of the areas where the PHJ33 hybrid will be grown. The PHJ33 hybrid has 10% higher yield and much better grain quality than 3324. disease tolerance of the PHJ33 hybrid will allow it to replace 3324 in the eastern Corn Belt.

TABLE 3

PAIRED INBRED COMPARISON DATA
INBRED #1 - PHJ33
INBRED #2 - PHV78

| YEAR | VAR # | BU ACR ABS | BU ACR % MN | BAR PLT ABS | BRT STK ABS | EAR HT ABS | EAR SZ ABS | EST CNT ABS | TIL LER ABS | GDU SHD ABS | GDU SLK ABS | GRN QUL ABS |
|---|---|---|---|---|---|---|---|---|---|---|---|---|
| TOTAL | 1 | 58.3 | 77 | 71.4 | 81.7 | 29.4 | 6.6 | 27.1 | 1.4 | 147.4 | 156.4 | 7.0 |
| SUM | 2 | 85.8 | 116 | 87.9 | 96.4 | 29.8 | 7.0 | 26.9 | 1.4 | 159.0 | 165.2 | 7.2 |
|  | LOCS | 2 | 2 | 13 | 5 | 14 | 16 | 68 | 20 | 65 | 64 | 3 |
|  | DIFF | 27.5 | 39 | 16.5 | 14.7 | 0.4 | 0.4 | 0.2 | 0.0 | 11.6 | 8.8 | 0.2 |
|  | PROB | .313 | .345 | .037+ | .378 | .802 | .111 | .748 | .985 | .000# | .000# | .893 |

| YEAR | VAR # | MST ABS | PLT HT ABS | POL WT ABS | POL WT % MN | POL SC ABS | RT LDG ABS | TAS BLS ABS | TAS SZ ABS | TAS WT ABS | TEX EAR ABS | TST WT ABS |
|---|---|---|---|---|---|---|---|---|---|---|---|---|
| TOTAL | 1 | 14.4 | 76.2 | 238.2 | 131 | 6.1 | 34.9 | 5.2 | 5.5 | 4.9 | 5.2 | 57.5 |
| SUM | 2 | 15.1 | 86.0 | 254.2 | 137 | 6.5 | 62.0 | 9.0 | 7.2 | 7.2 | 4.0 | 56.1 |
|  | LOCS | 2 | 15 | 6 | 6 | 34 | 1 | 3 | 28 | 6 | 13 | 2 |
|  | DIFF | 0.7 | 9.8 | 16.0 | 6 | 0.4 | 27.0 | 3.8 | 1.7 | 2.3 | 1.2 | 1.3 |
|  | PROB | .721 | .002# | .764 | .849 | .247 | .137 | .000# | .013+ | .015+ | .205 | |

| YEAR | VAR # | SCT GRN ABS | SDG VGR ABS | STA GRN ABS | STK CNT ABS | STK LDG ABS | YLD SC ABS | COM RST ABS | COM SMT ABS | EAR MLD ABS | ECB DPE ABS | ECB 1LF ABS |
|---|---|---|---|---|---|---|---|---|---|---|---|---|
| TOTAL | 1 | 4.8 | 5.2 | 5.4 | 25.2 | 100.0 | 4.9 | 4.5 | 0.0 | 5.7 | 70.0 | 5.3 |
| SUM | 2 | 5.5 | 5.1 | 6.0 | 25.1 | 98.9 | 6.1 | 4.5 | 1.0 | 5.0 | 73.3 | 6.0 |
|  | LOCS | 24 | 31 | 16 | 52 | 1 | 28 | 2 | 1 | 25 | 1 | 16 |
|  | DIFF | 0.7 | 0.1 | 0.6 | 0.1 | 1.1 | 1.2 | 0.0 | 1.0 | 0.7 | 3.3 | 0.8 |
|  | PROB | .066* | .761 | .098* | .770 | | .013+ | .000# | | .125 | | .052* |

| | YEAR | VAR # | ECB 2SC ABS | EYE SPT ABS | FUS EAR ABS | GLF SPT ABS | MDM CPX ABS | NLF BLT ABS | SLF BLT ABS | SO RST ABS | STW WLT ABS |
|---|---|---|---|---|---|---|---|---|---|---|---|
| TOTAL | | 1 | 4.6 | 5.0 | 33.1 | 4.6 | 2.8 | 6.0 | 6.6 | 7.0 | 8.0 |
| SUM | | 2 | 4.6 | 3.0 | 20.5 | 2.6 | 2.5 | 5.3 | 4.9 | 6.0 | 7.5 |
| | | LOCS | 6 | 1 | 4 | 6 | 2 | 5 | 6 | 1 | 2 |
| | | DIFF | 0.1 | 2.0 | 12.5 | 2.0 | 0.3 | 0.7 | 1.7 | 1.0 | 0.5 |
| | | PROB | .930 | | .195 | .012+ | .500 | .184 | .009# | | .795 |

\* = 10% SIG
+ = 5% SIG
# = 1% SIG

TABLE 4

Average Inbred by Tester Performance Comparing PHJ33 to PHV78 crossed to the same Inbred Tester and Grown in the Same Experiments. All Values are Expressed as percent of the experiment mean except Predicted RM, Selection Index, and Yield (Bu./Ac.).

| | Inbred | PRM | SEL IND | BU ACR | YLD | MST | GDU SHD | STK LDG | RT LDG | BAR PLT | STA GRN |
|---|---|---|---|---|---|---|---|---|---|---|---|
| TOTAL | REPLIC. | 29 | 29 | 51 | 51 | 51 | 9 | 50 | 17 | 4 | 33 |
| MEAN WTS | PHJ33 | 123 | 107 | 117 | 107 | 97 | 97 | 106 | 106 | 109 | 98 |
| MEAN WTS | PHV78 | 124 | 109 | 116 | 106 | 99 | 100 | 105 | 101 | 89 | 108 |
| | DIFF. | 2 | 1 | 1 | 1 | 2 | 3 | 1 | 5 | 20 | 10 |

| | Inbred | TST WTA | COB SC | GRN QUL | SDG VGR | EST CNT | PLT HT | EAR HT | DRP EAR | BRT STK |
|---|---|---|---|---|---|---|---|---|---|---|
| TOTAL | REPLIC. | 51 | 8 | 51 | 22 | 42 | 20 | 20 | 28 | |
| MEAN WTS | PHJ33 | 100 | 86 | 105 | 102 | 98 | 99 | 100 | 100 | |
| MEAN WTS | PHV78 | 100 | 76 | 100 | 110 | 99 | 97 | 100 | 100 | |
| | DIFF. | 0 | 10 | 5 | 7 | ·1 | 2 | 0 | 0 | |

The improved grain quality, higher yield and good

TABLE 5

1 - PHJ33 HYBRID
2 - PIONEER ® BRAND 3324

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL | | 1 | 123 | 110 | 152.1 | 110 | 22.8 | 146.4 | 94.3 | 76.4 | 100.0 | 5.8 |
| SUM | | 2 | 122 | 100 | 138.5 | 100 | 22.1 | 145.2 | 94.5 | 90.3 | 100.0 | 5.5 |
| | | LOCS | 16 | 15 | 83 | 83 | 83 | 16 | 75 | 20 | 1 | 45 |
| | | DIFF | 2 | 10 | 13.7 | 10 | 0.7 | 1.3 | 0.2 | 13.9 | 0.0 | 0.3 |
| | | PROB | .000# | .000# | .000# | .000# | .000# | .092* | .721 | .036+ | | .130 |

| | | | TST | COB | GRN | SDG | EST | STK | PLT | EAR | DRP |

TABLE 5-continued

1 - PHJ33 HYBRID
2 - PIONEER ® BRAND 3324

| YEAR | REGION | VAR # | WTA ABS | SC ABS | QUL ABS | VGR ABS | CNT ABS | CNT ABS | HT ABS | HT ABS | EAR ABS |
|---|---|---|---|---|---|---|---|---|---|---|---|
| TOTAL SUM | | 1 | 56.6 | 3.0 | 7.3 | 5.8 | 57.0 | 49.3 | 96.3 | 45.4 | 99.9 |
| | | 2 | 55.9 | 4.0 | 6.3 | 5.9 | 56.8 | 49.6 | 94.2 | 44.4 | 99.6 |
| | | LOCS | 82 | 1 | 75 | 24 | 69 | 83 | 27 | 37 | 61 |
| | | DIFF | 0.7 | 1.0 | 1.0 | 0.2 | 0.2 | 0.3 | 2.1 | 1.0 | 0.3 |
| | | PROB | .000# | | .000# | .281 | .621 | .383 | .008# | .026+ | .019+ |

* = 10% SIG
+ = 5% SIG
# = 1% SIG

Applicants have made available to the public without restriction a deposit of at least 2500 seeds of inbred PHJ33 with the American Type Culture Collection (ATCC), Tockville, Md. 20852 USA, ATCC Deposit No. 75072. The seeds deposited with the ATCC are taken from the same deposit maintained by Pioneer Hi-Bred International Inc., 700 Capital Square, 400 Locust Street, Des Moines, Iowa 50309 since prior to the filing date of this application. The deposit will be maintained in the ATCC depository, which is a public depository, for a period of 30 years, or 5 years after the most recent request, or for the effective life of the patent, whichever is longer, and will be replaced if it becomes nonviable during that period.

What is claimed is:

1. Inbred corn seed designated PHJ33 having ATCC accession No.
2. A corn plant produced by the seed of claim 1.
3. Tissue culture of the plant of claim 2.
4. Tissue culture according to claim 3 comprising regenerable cells of a plant part selected from meristematic tissue, anthers, leaves, embryos, protoplasts, and pollen.
5. A corn plant regenerated from the regenerable cells of a tissue culture according to claim 4.
6. An inbred corn plant having all the physiological and morphological characteristics of the seed of claim 1.

* * * * *